United States Patent [19]

Barrett

[11] Patent Number: 4,865,026
[45] Date of Patent: Sep. 12, 1989

[54] SEALING WOUND CLOSURE DEVICE

[76] Inventor: David M. Barrett, P.O. Box 1693, Oklahoma City, Okla. 73101

[21] Appl. No.: 42,116

[22] Filed: Apr. 23, 1987

[51] Int. Cl.$^4$ ................. A61F 13/00; A61F 15/00
[52] U.S. Cl. ................................. 128/155; 128/335; 128/95.1; 128/857; 128/890; 604/307; 450/81
[58] Field of Search ............... 128/76.5, 95.1, 97.1, 128/112.1, 119.1, 132 R, 149, 150, 155, 156, 163, 335, 846, 847, 848, 889, 890; 450/81; 604/304, 307; 623/1, 66

[56] References Cited

U.S. PATENT DOCUMENTS

| | | | |
|---|---|---|---|
| 1,920,808 | 8/1933 | Sander | 128/156 |
| 1,956,695 | 5/1934 | Reinitz | 128/155 |
| 3,026,874 | 3/1962 | Stevens | 604/305 |
| 3,297,036 | 1/1967 | Williams | 450/81 |
| 4,430,998 | 2/1984 | Harvey et al. | 128/335 |
| 4,577,631 | 3/1986 | Kreamer | 128/334 R |
| 4,641,641 | 2/1987 | Strock | 128/846 |
| 4,706,661 | 11/1987 | Barrett | 128/155 |
| 4,709,695 | 12/1987 | Kohn et al. | 128/132 R |
| 4,710,192 | 12/1987 | Liotta et al. | 623/1 |

Primary Examiner—Richard J. Apley
Assistant Examiner—Paul Prebilic

[57] ABSTRACT

The device comprises a resilient, annular, adhesive-backed planar pad with a central opening, and a resilient protective covering which overlies this central opening. A manually operated control device is used to spread the resilient pad radially prior to the application of the device to the skin around a wound. The control device is then released to permit the pad and resilient covering to contract, thereby drawing together the opposing edges of the wound. The covering shields the wound from contamination, and the wound closure device additionally restricts residual bleeding by virtue of the adhesive sealing action provided. The covering defines a chamber or space over the wound which can contain medication, and the covering can be made transparent to permit observation of the wound without the necessity of removal of the wound-closing device. Further the covering can be made independently removable to permit access to the wound area, without necessating removing the wound closing device nor necessating disruption to the devices wound closing forces.

10 Claims, 4 Drawing Sheets

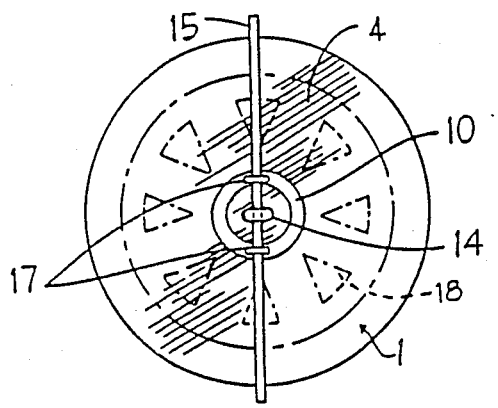
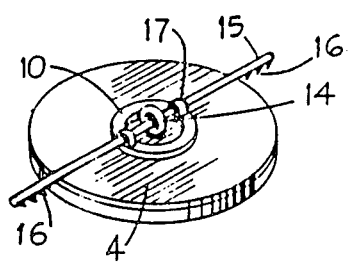
FIG. 7
FIG. 8
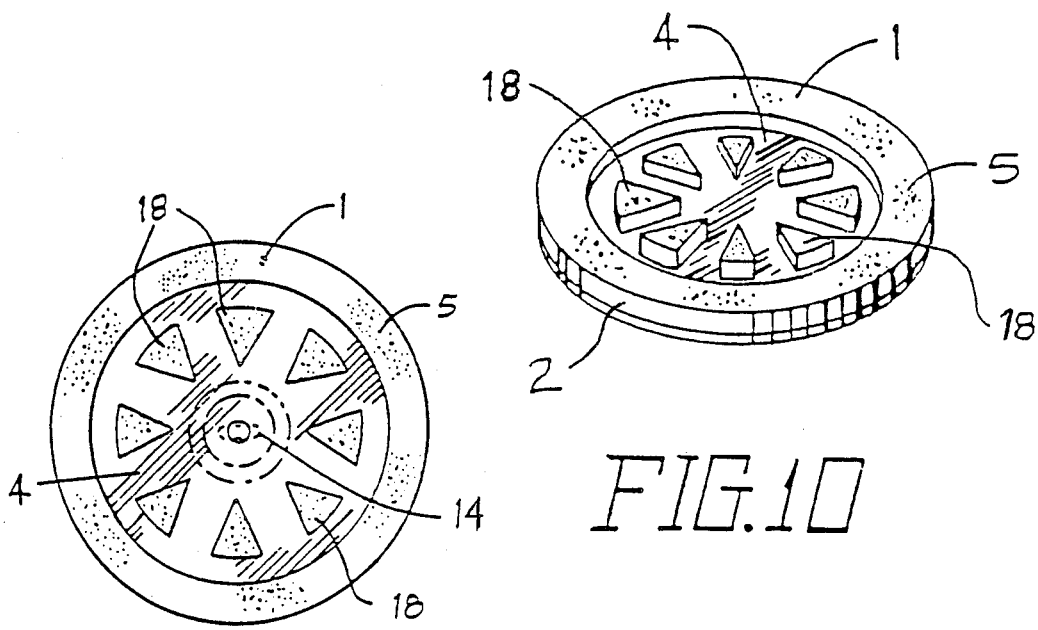
FIG. 9
FIG. 10
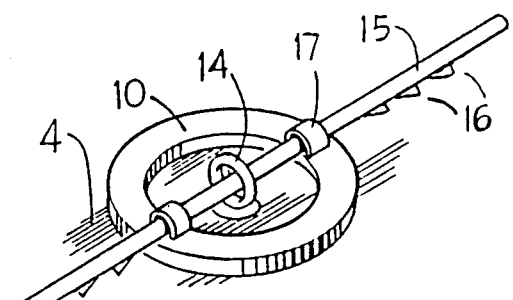
FIG. 11

SEALING WOUND CLOSURE DEVICE

FIELD OF THE INVENTION

This invention relates to medical supplies, including, but not limited to, the following:

(1) First aid devices, and, (2) Surgical bandaging. This invention is moreover particularly applicable as a wound-closing device for punctures through the skin, including such injuries which cause tissue removal, or those which involve sores of the ulcer or lesion variety.

DESCRIPTION OF THE PRIOR ART

Adhesives strips of the first aid type have usually comprised a single section or length of material having a backing sheet or pad above an overlying resilient pad with adhesive material on respective opposing end portions of the bandage. These have proven most satisfactory for very small wounds, not too deep into the skin, in that the pad tends to cling to a bleeding wound, resulting in reopening the wound when the adhesive strip is removed for dressing the injury, as the scab is removed along with the pad to which it is now attached.

Surgical bandaging traditionally has begun with a larger pad of gauze material, which is then attached to the tissues surrounding a wound with adhesive tape, and reinforced with wrappings of additional adhesive tape. Such bandaging only covers a wound: it cannot help in positioning the tissues for healing by holding opposing edges of a wound together in optimal positions for healing. The gauze pad, like the pad of adhesive-strip type bandaging, clings to bleeding wounds and can reopen such wounds by pulling the scab off the wound during removal of the bandaging.

All such direct contact bandages tend to fill into and separate tissues which would heal better if allowed to join without the added contamination of, or interference from, contact type bandages. In addition, the pulling of skin during the removal of the adhesive strip or adhesive tape may tend to pull wound edges apart, opening the wound to more bleeding.

SUMMARY OF THE INVENTION

This invention provides a device which eliminates, or reduces the effect of, the preceding delineated disadvantages, and which provides the capability of accurate placement by remote control or direct manual application, employing physical and/or adhesive attachment to the periphery of a wound. The device of the invention includes a continuous substantially circular or annular adhesive strip or pad which, when stressed or prestressed (i.e., stressed prior to application) through an associated, preferably resilient protective cover, tends to pull the tissue together to provide closing of a puncture wound or a wound with missing tissue. The device of the invention provides a sealing action around the wound so as to restrict bleeding without the necessity for direct contact with the wound itself and may permit visual observation thereof during healing. The device of the invention permits the unrestricted passage of air to the wound while covering the wound and while preventing contamination thereof as well as preventing aggravating physical contact. The device of the invention permits access to the wound without removal of the device's wound-closing ability.

In one embodiment, a substantially circular or annular pad of rectangular transverse cross section is provided, having one surface coated with adhesive material (adapted to be attached to a patient's skin). A protective covering is secured to the opposite surface thereof. This protective covering has an equal diameter to the pad, which includes multiple opposing flanges. These flanges are used with angular members which engage the pad for placing the latter over a wound.

In another embodiment a plurality of further adhesive pads are used in addition to the circular adhesive pad. Additionally, this particular embodiment provides for distribution of part of the wound closing force to be applied below the surface of the skin in order to facilitate closure of deeper wounds.

In a further embodiment both pins and adhesive are used and the pin elements are physically removable from the pads. With this arrangement, after the device has been properly applied and aligned, and the forces acting to close the wound have acted to draw the tissue adjacent to the wound closer together and healing has begun, the forces necessary to maintain the device in place are reduced and the adhesive attachments are sufficient so that the pins can be withdrawn. The pins can also be removed or withdrawn at a point in time where surgical procedures have provided a secure closure.

In all embodiments, the resilient material may be prestressed and held in such stress by a removable circular expander which, when inserted in place, provides radial expansion of the device.

The principal objects of this invention are to provide a wound protecting device which is self-adhering or attaching, which tends to draw together opposing edges of a wound, i.e., to draw these edges toward each other from opposing positions laterally of the boundary of the wound; which provides for cessation of blood loss; which achieves a consistent, even pressure along the periphery of the wound as well as allows the blood pressure itself to become pressure-neutralized against any outward flow, by virtue of the physical containment provided by the resilient pad or strip; which does not constrict blood circulation or capillary blood flow; which enables aeration of the wound during healing as well as provides for visual observation of the wound; and which provides for access to the wound without removal of the established wound closure force.

DESCRIPTION OF THE DRAWINGS

FIG. 7 is a top plan view of a further embodiment of the invention which is adapted to increase the natural resilient tendency of the device to facilitate closing of a wound and which is designed for use after the device has been attached to the patient;

FIG. 8 is a top perspective view of FIG. 7;

FIG. 9 is a bottom plan view of FIG. 7.

FIG. 10 is a bottom perspective view of FIG. 7, also indicating the pad depth or height;

FIG. 11 is a detailed view, on an enlarged scale, of the central section of FIG. 8;

DESCRIPTION OF THE PREFERRED EMBODIMENTS

Figure 1:
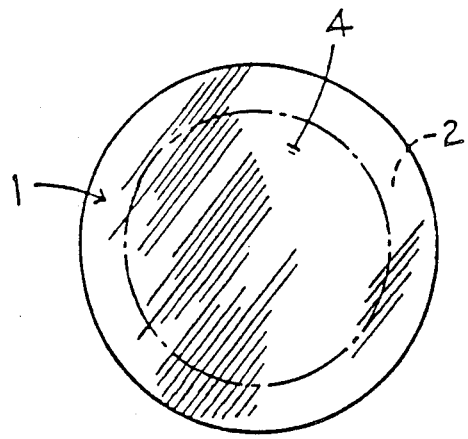
FIG. 1 is a top plan view of one embodiment of the device of the invention.

In the drawings, like references designate like parts in the drawings in which they occur.

Figure 2:
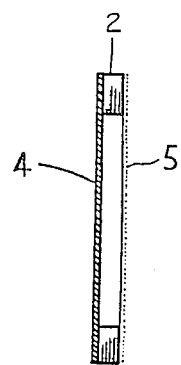
FIG. 2 is a cross-sectional view of FIG. 1.

Referring to FIGS. 1 and 2, a first embodiment of the protective wound closure device of the invention is shown. The device, which is generally denoted 1, includes a pad, 2, of substantially circular or annular shape which, as shown in FIG. 2, is substantially rectangular in cross section and includes an upper generally planar surface to which an overlying protective covering or cover, 4, is releasably secured and a planar base surface. Pad, 2, is made of resilient material and is adapted to be affixed or attached to a wound site by an adhesive layer, 5, applied to the base surface of pad, 2. Cover, 4, can also be constructed of resilient material.

Figure 3:
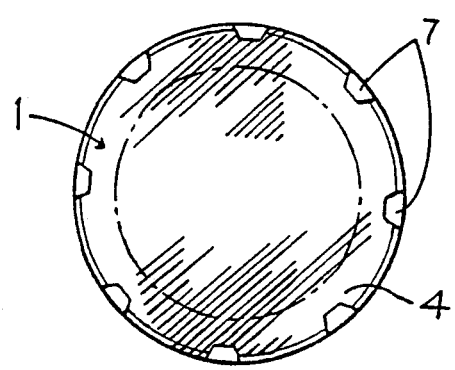
FIG. 3 is a top plan view of a second embodiment of the invention wherein the device of the invention includes multiple opposing flange members which facilitate spreading apart of the circular pad.
Figure 4:
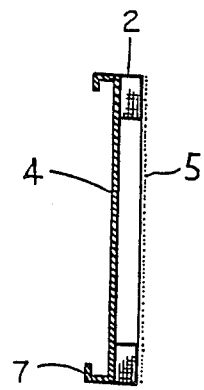
FIG. 4 is a cross sectional view of FIG. 3.
Figure 5:
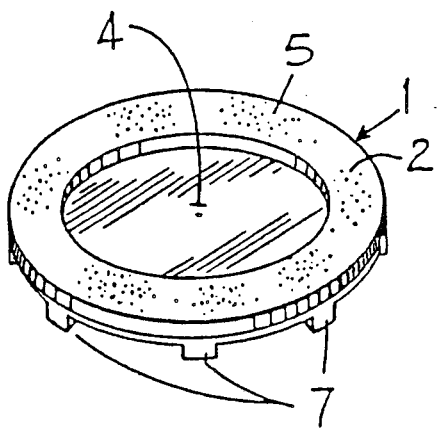
FIG. 5 is a bottom perspective view of FIG. 3.

Referring to FIGS. 3 to 5, a further embodiment is shown which is similar to that of FIGS. 1 and 2 except that hook-like engagement flanges, 7, of an inverted L shape are formed integrally with cover, 4, and disposed in equally-spaced relation around the periphery thereof.

Figure 6:
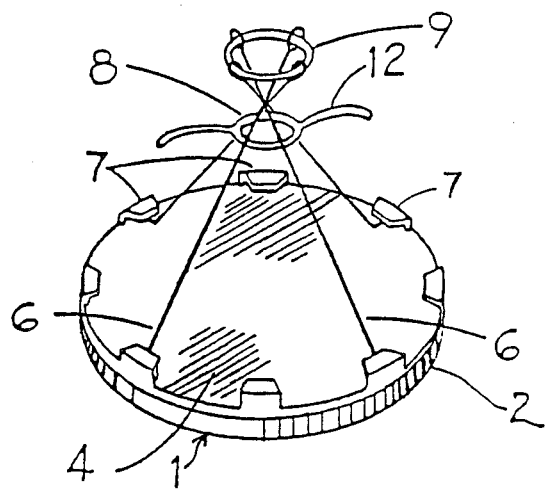
FIG. 6 is a top perspective view of FIG. 3 with the addition of a control device for spreading the pad apart, i.e., for increasing the diameter of the circular pad.

Referring to FIG. 6, an expandable control device for providing expansion or spreading apart of the closure device, 1, is shown in place on the cover, 4, of the closure device, 1. The control device includes control arms, 6, which are disposed in diagonal, crossing relationship, and which are individually attached at one end to an upper control ring, 9, and at the other end to the engagement hooks or flanges, 7, of the wound closure device, 1. A further, lower control ring, 8, encircles the control rods, 6, and includes handles or finger grips, 12.

By holding the handles, 12, of lower ring, 8, and pressing downwardly on upper ring, 9, upper ring, 9, is brought closer to ring, 8, and control arms, 6, are caused to spread laterally, thereby exerting radially outwardly directed forces on corresponding engagement flanges, 7. This provides radial expansion of pad member, 2, and corresponding prestressing of the resilient elastic material of cover, 4, prior to application of the closure device, 1, to a patient.

Referring to FIGS. 7 to 11, a further embodiment of the invention is shown. The wound closure device, 1, of FIG. 7 is basically the same as described previously, except for the addition of a plurality of pie-shaped pads, 18, which are located radially inwardly toward the center of the device. These pads, 18, which are referred to as "conjunctive" pads, act in conjunction with annular pad, 2, to assist in drawing the wound tissue together.

The embodiment of FIGS. 7 to 11 further includes an elevating mechanism for lifting the central segment or portion of cover, 4, above the normal plane thereof to centrally contract cover, 4, and to also increase the closure forces on pad, 2, and pads, 18, and so as to further enhance the drawing together of the wound tissue. This elevating mechanism includes an eyelet, 14, attached to the resilient elastic cover, 4. A flexible arm or rod, 15, extends through eyelet, 14, and is supported on a retaining ring, 10, by retaining collars, 17. A series of downwardly extending teeth, 16, serve to secure the elevating or lifting arrangement in place after, for example, a hook (not shown) has been used to lift eyelet, 14, to a plane above the normal plane thereof, i.e., for maintaining resilient cover, 4, in the elevated position thereof.

Figure 12:
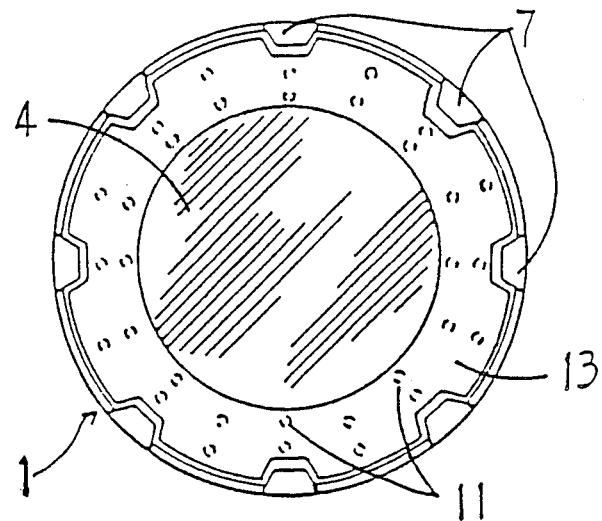
FIG. 12 is a top plan view of a device in accordance with a fourth embodiment of the invention.
Figure 13:
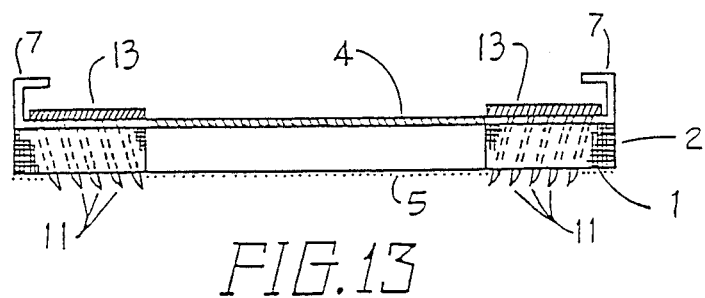
FIG. 13 is a cross sectional view, on an enlarged scale, of FIG. 12.

Referring to FIGS. 12 and 13, a further embodiment is shown which is similar to that of FIGS. 1 to 11, but which uses pins, 11, to attach or secure the device, 1, to the wound site, and which includes an annular base plate, 13, to which pins, 11, are attached. This arrangement enables pins, 11, to be withdrawn or removed without necessitating removal of the pad, 2.

Figure 14:
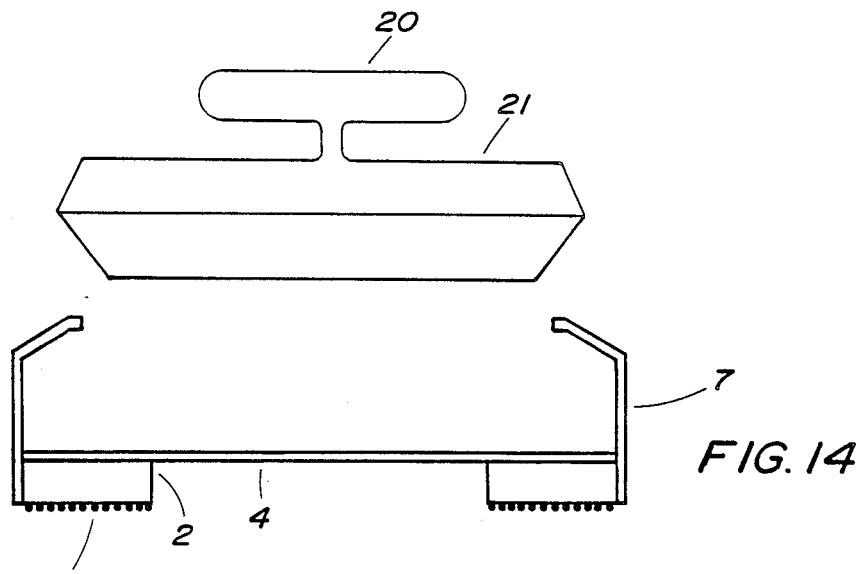
FIG. 14 is a diagrammatic side of a further embodiment of the invention.
Figure 15:
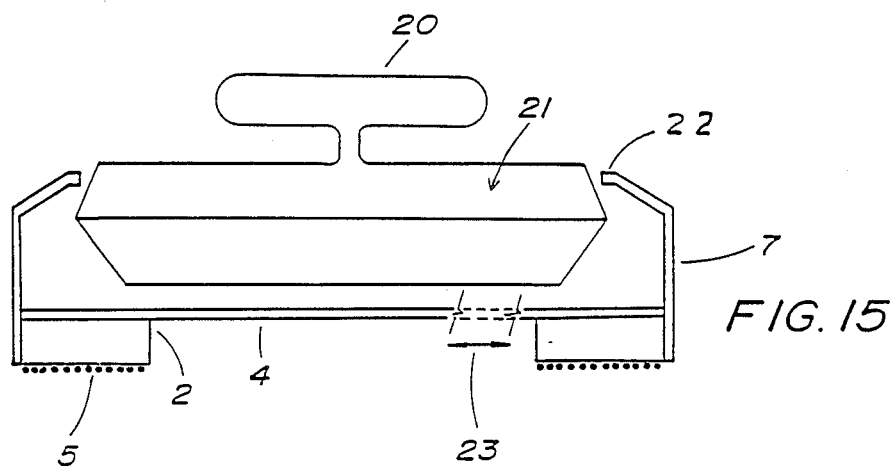
FIG. 15 is a view similar to FIG. 14 showing a further stage in the use of the device; and, FIG. 16 is a view similar to FIG. 14 showing a final stage in the use of the device.
Figure 16:
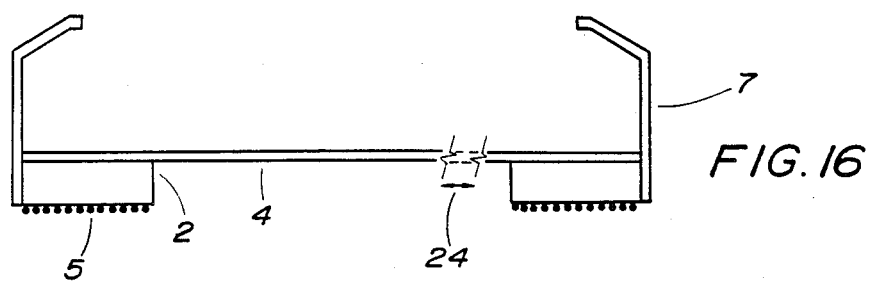

Referring to FIGS. 14 to 16, a further embodiment of the invention is shown. In this embodiment, a generally circular shaped stressing member or unit, 21, having an attached handle, 20, is shaped to be received, as shown in FIG. 14, between elongated hooks, 22, which are secured to wound closure device, 1, so as to force hooks, 22, apart and thus cause expansion of pad, 2, and stretching of resilient cover, 4, as indicated at 23. The closure device, 1, is then applied to the wound site, and the stressing member, 21, is removed so that pins, 11, shown in the embodiment of FIGS. 12 and 13 are used together with the adhesive, 5, of FIGS. 1 to 11, engage the skin of the patient and provide holding of the device, 1, in place on the wound site. With stressing member, 21, then removed as shown in FIG. 6, the pins, 11, are drawn inwardly to provide firm engagement with the skin and tissue surrounding the wound, and the residual stretching of cover, 4, which is indicated at 24, serves to maintain this attachment.

OPERATION

In the use of the adhesive-backed embodiment of FIGS. 1-6, the device as shown in FIG. 6 is removed from its container, not shown at the point of use. The operator grasps the controlling portion or handle, 12, of the control device of FIG. 6 between the forefinger and middle finger and places the thumb or palm of the hand on the control ring, 9, and manually moves the control ring downwardly in a converging action, which fulcrums the control arms, 6, against the control ring, 8, thereby forcing the control arms, 6, radially outward in opposing directions. This causes the spreading of the closure device, 1, laterally apart to the desired extension of the elastic pad member, 2, in accordance with the lateral dimension of the wound or puncture, or to the limit of the length of the control arms, 6.

The operator then places the closure device, 1, in straddling relation around the wound, such as a puncture, with the pad member, 2, contacting the patient's skin, and thereafter releases the pressure on the control ring, 9. This action (the release of pressure) allows the control arms, 6, to retract from contact with the respective hook or engagement flange members, 7, and enables separation of the control device from the wound closure device, 1. The circular elastic cover strip or covering, 4, by virtue of its resiliency, draws the circular pad, 2, inward toward the center in a wound closing action without necessitating contact between the central portion of the cover strip, 4, and the surface of the wound.

Referring now to the embodiment of FIGS. 7 through 11, as described above, the closure device of this embodiment is similar to that of FIGS. 1 to 6 but, in addition, includes a plurality of conjunctive pads, 18, which are of a similar adhesive-coated material to pad, 2, and which are arranged so as to be directed toward the center of device 1 and to lie in a common plane with the plane of the annular or circular planar pad, 2. The pads, 18, are connected together by the overlying resilient cover, 4, which, when flexed, similarly tends to draw the inwardly directed or confronting edges of the several pads, 18, toward their common center.

In addition, in this embodiment, the wound closing action is enhanced by altering the position of the resilient elastic covering, 4, by raising the central portion of covering, 4, to a plane above the normal plane thereof, after application of the device, 1. This alteration of position, i.e., this lifting action, is accomplished by eyelet means, 14, and the covering, 4, is secured in this elevated position by means of the non-connected ring, 10, in cooperation with flexible transverse rod, 15, which extends through eyelet, 14, and which is secured to ring, 10, by retaining collars, 17. With this arrangement, when eyelet, 14, is raised by suitable means, such as the hook (not shown) referred to above so as to lift a portion of the resilient elastic covering, 4, to a plane above the normal plane thereof, the securing teeth, 16, can be used to engage the unattached ring, 10, and thereby secure covering, 4, in this elevated position. When the arrangement is thus secured, the increased stress on the resilient elastic covering, 4, will act primarily on the conjunctive pads, 18, and secondarily on the outer annular pad, thereby creating an additive effect to enhance the closure forces to a greater extent on pads, 18, which are closer to the wound and to a lesser extent on outer annular pad 2, thereby to augment the wound closure by this action.

Referring now to FIGS. 12 and 13, in this embodiment, as described above, physical attachment of the closure device to the patient is provided by pins, 11, affixed to the pin base plate, 13, and protruding downward through the annular pad, 2, at such an angle as to privide entry thereof into the patient's skin in response to the contracting forces exerted by annular pad, 2, and elastic covering, 4, so as to physically secure wound closure device, 1, in place around the periphery of the wound.

These attachment pins, 11, in combination with the attachment adhesive, 5, insure the sealing action of the annular pad, 2, around the periphery of the wound, and thereby prevent, by means of this sealing action, external blood loss. Thus the device tends to stop bleeding without direct contact with the wound itself.

Referring now to the embodiment of FIGS. 14, 15, and 16, elongated hook flanges, 22, are used to accept, prior to application of the wound closure device, 1, stress on the resilient elastic covering, 4, as provided by stressing member, 21, received therebetween. With this arrangement, resilient covering, 4, is prestressed and thus stretched or expanded by an amount indicated at 23. Thereafter, with insertion unit, 21, removed by means of handle, 20, and in conjunction with the insertion of pins, 11, into the periphery of the wound, covering, 4, contracts but is still stretched or expanded by a relative amount indicated at 24. Thus, this embodiment provides a form of prestressing application device for the application of the basic protective wound closure device, 1.

Obviously the invention is susceptible to changes or alterations without defeating its practicability, and is not limited to the preferred embodiments described above and shown in the accompanying drawings. The height above the wound is essential to medication holding and exchange, as is removal of protective cover regarding positioning or repositioning while insuring non-contact with the wound. However, this height above the wound is not critical to the invention nor is the elasticity of the center piece or use of mechanical means to simultaneously draw inward from the attached edges to the center.

Although the present invention has been described relative to exemplary embodiments thereof, it will be understood by those skilled in the art that variations and modifications can be effected in these exemplary embodiments without departing from the scope and spirit of the invention.

I claim:

1. A wound closure device comprising a substantially annular pad member having opposed,
   substantially planar surfaces, and central opening therethrough;
   a protective covering releasably secured to one planar surface of said pad member;
   said annular pad member being formed from resilient material, capable of being expanded to surround a wound whereby when said pad member is permitted to relax, its resilience acts to draw together the tissue surrounding the wound to assist in providing closure of the wound;
   expansion means including flanges attached to the periphery of
   said device at circumferentially spaced locations for expanding said annular resilient pad member;
   said expansion means further including a control device having at least two arms for releasably engaging respective said flanges, adjustment means for providing a spreading movement of said arms away from each other to provide radial expansion of the closure device; and handle means for engaging said expansion means to provide radial expansion of said annular resilient pad member such that release of said handle means will enable radial contraction of said annular resilient pad member; and,
   an affixing means, secured to the surface opposite said one surface of the annular pad member for affixing the device to skin of a patient having a wound or ulceration such that the wound is positioned within said central opening.

2. A device as claimed in claim 1 wherein said arms are disposed in crossed relationship and
   said control device further includes:
   a first upper control ring having one end of each of said arms attached thereto,
   said adjustment means including an adjustable lower control ring, surrounding and movable along the lengths of said arms, to induce the spreading movement of the ends of said arms opposite said one end of each arm.

3. A wound closure device comprising a substantially annular pad member having opposed, substantially planar surfaces, and a central opening therethrough;
   a protective covering releasably secured to one planar surface of said pad member;

an affixing means, secured to the surface opposite said one surface of the annular pad member for affixing the device to skin of a patient having a wound or ulceration such that the wound is positioned within said central opening, said affixing means comprises;

an adhesive; and, a plurality of removable pins.

4. A wound closure device comprising a substantially annular pad member having opposed, substantially planar surfaces, and a central opening therethrough;

a protective covering releasably secured to one planar surface of said pad member;

said annular pad member being formed from resilient material, capable of being expanded to surround a wound whereby when said pad member is permitted to relax, its resilience acts to draw together the tissue surrounding the wound to assist in providing closure of the wound;

an affixing means, secured to the surface opposite said one surface of the annular pad member for affixing the device to the skin of a patient having a wound or ulceration such that the wound is positioned within said central opening; and, a plurality of additional resilient pad members disposed radially inward from the inner perimeter of said annular pad member.

5. A device as claimed in claim 4 wherein;

said protective covering comprises an elastic cover; and force exerting means for exerting additional closure forces to said pad member after said device has been applied to a wound site to further draw together the tissues around the wound and enhance closure of the wound.

6. A device as claimed in claim 5 wherein said force exerting means comprises:

an eyelet attached to said protective cover;

an operating rod extending through said eyelet, for maintaining the eyelet in an elevated position and maintaining the portion of the protective cover to which the eyelet is attached in an elevated position.

7. A wound closure device comprising a substantially annular pad member having opposed, substantially planar surfaces, and a central opening therethtough;

a protective covering releasably secured to one planar surface of said pad member;

said annular pad member being formed resilient material, capable of being expanded to surround a wound whereby when said pad member is permitted to relax, its resilience acts to draw together the tissue surrounding the wound to assist in providing closure of the wound; an affixing means, secured to the surface opposite said one surface of the annular pad member for affixing the device to the skin of a patient having a wound or ulceration such that the wound is positioned within said central opening;

expansion means for expanding said annular resilient pad member having handle means for manually operating said expansion means; said expansion means engaging said annular resilient pad member to provide radial expansion of said annular resilient pad member such that release of said handle means will enable radial contraction of said annular resilient pad member; said expansion means further comprises an upper control ring which, when moved toward said protective covering exerts expansion forces on said annular resilient pad.

8. In combination, a wound closure device with means for applying the wound closure device to a wound site, said wound closure device comprising: a substantially annular, resilient pad having a central opening therethrough;

an overlying removable protective covering on said annular resilient pad;

means for affixing the device to a wound site with the wound site surrounded by the central opening in said pad member;

said applying means including releasable means for expanding said resilient pad member such that, upon release of the releasable means said resilient pad member contracts radially, thereby drawing together the tissues adjacent to the wound to assist in providing closure of the wound, and, said applying means further includes:

a plurality of flanges disposed in spaced relation around around the periphery of said annular resilient pad, wherein said applying means includes arm means engaging said flanges for exerting radially outward acting force on said annular resilient pad and radial expansion thereof.

9. The combination as claimed in claim 8 wherein said applying means comprises:

upper and lower control rings engaging said arm means which, when said arm means are inserted into engagement with said releasable means provides radial expansion of said annular resilient pad.

10. A circular wound closure and protective device comprising:

(a) a circular elastic planar pad with a concentric hole forming an annulus;

(b) said circular elastic planar pad having an adhesive coating on a front face thereof;

(c) elastic material overlying and covering both a back face and the annulus of said circular elastic planar pad;

(d) an expansion means including at least two radially aligned flanges protruding generally normal to the plane of the circular elastic planar pad, said flanges being attached to the outer perimeter of the circular elastic planar pad;

(e) said flanges being adapted to receive a releasable controlling means for radially stretching the device before it is adhesively applied to skin surrounding a wound, so that when the releasable controlling means is released said device will elastically contract and act to close the wound.

* * * * *